(12) United States Patent
Solf et al.

(10) Patent No.: US 8,897,518 B2
(45) Date of Patent: Nov. 25, 2014

(54) FUNCTIONAL IMAGING (75) Inventors: Torsten Solf, Aachen (DE); Bernd Schweizer, Herzogenrath (DE); Martin Weibrecht, Aachen (DE); Carolina Ribbing, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 464 days.

(21) Appl. No.: 13/202,840

(22) PCT Filed: Feb. 9, 2010

(86) PCT No.: PCT/IB2010/050579
§ 371 (c)(1),
(2), (4) Date: Aug. 23, 2011

(87) PCT Pub. No.: WO2010/106449
PCT Pub. Date: Sep. 23, 2010

(65) Prior Publication Data
US 2011/0299747 A1 Dec. 8, 2011

Related U.S. Application Data (60) Provisional application No. 61/161,433, filed on Mar. 19, 2009, provisional application No. 61/237,048, filed on Aug. 26, 2009.

(51) Int. Cl.
*G06K 9/00* (2006.01)
*A61B 6/00* (2006.01)
*A61B 6/03* (2006.01)
*A61B 8/00* (2006.01)
*G06F 19/00* (2011.01)
*A61B 5/00* (2006.01)
*A61B 5/055* (2006.01)
*A61B 8/08* (2006.01)

(52) U.S. Cl.
CPC . *A61B 6/00* (2013.01); *A61B 6/037* (2013.01); *A61B 6/463* (2013.01); *A61B 6/545* (2013.01); *A61B 8/463* (2013.01); *A61B 8/585* (2013.01); *G06F 19/321* (2013.01); *G06F 19/3487* (2013.01); *A61B 5/743* (2013.01); *A61B 5/055* (2013.01); *A61B 8/481* (2013.01)
USPC .......................................................... 382/128

(58) Field of Classification Search
USPC ................................................. 382/128–132
See application file for complete search history.

(56) References Cited

U.S. PATENT DOCUMENTS 6,478,735 B1 * 11/2002 Pope et al. .................... 600/300
6,690,371 B1    2/2004 Okerlund et al.
(Continued)

FOREIGN PATENT DOCUMENTS

EP    1536364 A2    6/2005
JP    H05168606 A    7/1993
(Continued)

OTHER PUBLICATIONS

Boellaard, et al., The Netherlands protocol for standarization and quantification of FDG whole body PET studies in multi-centre trials, European J. Nucl. Med. and Molec. Imag., Dec. 2008, pp. 2320-2333, vol. 35, issue 12, abstract attached.

*Primary Examiner* — Aaron W Carter (57) ABSTRACT

A method includes obtaining an image of a region of interest of a subject, wherein the image is generated with image data produced by an imaging system used to scan the subject, obtaining a signal indicative of a physiological state of the subject before the scan, and displaying both the image and data indicative of the physiological state. In another aspect, a method includes correcting, via a processor, a tracer uptake value for a target region of interest based on a tracer uptake correction factor.

20 Claims, 7 Drawing Sheets

(56) References Cited

U.S. PATENT DOCUMENTS

| | | | |
|---|---|---|---|
| 6,853,854 B1 * | 2/2005 | Proniewicz et al. | 600/319 |
| 6,937,696 B1 * | 8/2005 | Mostafavi | 378/95 |
| 7,327,862 B2 * | 2/2008 | Murphy et al. | 382/128 |
| 7,569,015 B2 * | 8/2009 | Donaldson et al. | 600/437 |
| 7,775,978 B2 * | 8/2010 | Nadadur et al. | 600/437 |
| 7,847,251 B1 * | 12/2010 | Praly | 250/330 |
| 7,867,477 B2 | 1/2011 | Driehuys et al. | |
| 7,869,848 B2 * | 1/2011 | Proniewicz et al. | 600/319 |
| 8,050,476 B2 * | 11/2011 | Dentinger | 382/131 |
| 8,055,045 B2 * | 11/2011 | Kokubun et al. | 382/131 |
| 8,150,112 B2 * | 4/2012 | Kadir et al. | 382/128 |
| 8,164,672 B2 * | 4/2012 | Meron et al. | 348/333.05 |
| 8,208,987 B2 * | 6/2012 | Hengerer et al. | 600/411 |
| 8,488,857 B2 * | 7/2013 | Young et al. | 382/131 |
| 8,615,116 B2 * | 12/2013 | Lardo et al. | 382/128 |
| 2004/0005273 A1 * | 1/2004 | Driehuys et al. | 424/9.3 |
| 2004/0064037 A1 * | 4/2004 | Smith | 600/420 |
| 2004/0077952 A1 | 4/2004 | Rafter et al. | |
| 2004/0102693 A1 * | 5/2004 | Jenkins | 600/410 |
| 2005/0096530 A1 * | 5/2005 | Daw et al. | 600/408 |
| 2005/0201510 A1 * | 9/2005 | Mostafavi | 378/8 |
| 2006/0164511 A1 * | 7/2006 | Krupnik | 348/65 |
| 2007/0016028 A1 * | 1/2007 | Donaldson et al. | 600/437 |
| 2007/0016029 A1 * | 1/2007 | Donaldson et al. | 600/437 |
| 2007/0050715 A1 * | 3/2007 | Behar | 715/706 |
| 2007/0066892 A1 * | 3/2007 | Haras et al. | 600/425 |
| 2007/0230893 A1 * | 10/2007 | Meron et al. | 386/4 |
| 2008/0009723 A1 * | 1/2008 | Schefelker et al. | 600/437 |
| 2008/0056547 A1 * | 3/2008 | Kokubun et al. | 382/128 |
| 2008/0056550 A1 * | 3/2008 | Kadir et al. | 382/131 |
| 2008/0084961 A1 * | 4/2008 | Keppel et al. | 378/37 |
| 2008/0131362 A1 | 6/2008 | Rousso et al. | |
| 2008/0230705 A1 * | 9/2008 | Rousso et al. | 250/363.04 |
| 2009/0018438 A1 * | 1/2009 | Schroder et al. | 600/431 |
| 2009/0067699 A1 * | 3/2009 | Clark | 382/131 |
| 2009/0082658 A1 * | 3/2009 | Hamilton et al. | 600/410 |
| 2009/0117044 A1 | 5/2009 | Hengerer et al. | |
| 2009/0269278 A1 * | 10/2009 | Burns et al. | 424/1.89 |
| 2009/0292551 A1 * | 11/2009 | Sirohey et al. | 705/2 |
| 2009/0292557 A1 * | 11/2009 | Sirohey et al. | 705/3 |
| 2010/0092051 A1 * | 4/2010 | Kadir et al. | 382/128 |
| 2010/0135556 A1 * | 6/2010 | Razifar et al. | 382/131 |
| 2010/0152577 A1 * | 6/2010 | Young et al. | 600/431 |
| 2010/0196264 A1 * | 8/2010 | Drum | 424/1.11 |
| 2010/0260402 A1 * | 10/2010 | Axelsson et al. | 382/131 |
| 2010/0317967 A1 | 12/2010 | Carlsen et al. | |
| 2011/0082368 A1 * | 4/2011 | Botterweck | 600/425 |
| 2011/0089326 A1 * | 4/2011 | Falen et al. | 250/363.04 |
| 2011/0148861 A1 * | 6/2011 | Boellaard | 345/419 |
| 2011/0299747 A1 * | 12/2011 | Solf et al. | 382/128 |
| 2012/0071771 A1 * | 3/2012 | Behar | 600/508 |
| 2013/0024126 A1 * | 1/2013 | Weibrecht | 702/19 |

FOREIGN PATENT DOCUMENTS

| | | |
|---|---|---|
| JP | 2008061766 A | 3/2008 |
| JP | 2008067931 A | 3/2008 |
| WO | 2008062384 A1 | 5/2008 |
| WO | 2008155738 A2 | 12/2008 |

* cited by examiner

FUNCTIONAL IMAGING

CROSS REFERENCE TO RELATED APPLICATIONS

This application claims the benefit of U.S. provisional application Ser. No. 61/161,433 filed Mar. 19, 2009 and U.S. provisional application Ser. No. 61/237,048 filed Aug. 26, 2009, both of which are incorporated herein by reference.

The following generally relates to imaging and finds particular application to functional PET imaging. However, it is also amenable to other imaging modalities, including functional and non-functional imaging.

Functional imaging provides information related to changes in metabolism, blood flow, and absorption. However, the physiological state and/or the behavioral state of a subject may affect the quantitative information in the resulting images and thus the interpretation of the images. By way of example, with F-18-FDG-PET, the radioactive tracer FDG (fluorodeoxyglucose) is administered to the patient. The patient is then asked to lie still (e.g., for sixty (60) to ninety (90) minutes) and not consume any food while the administered FDG is taken up and distributed in the body and until after the scan.

The administered FDG, which includes a radioactive sugar, is taken up by glucose using cells such as brain, kidney and cancer cells. The taken up FDG undergoes radioactive decay and produces positrons. When such a positron interacts with an electron in a positron annihilation event, a coincident pair of 511 keV gamma rays is generated. The gamma rays travel in opposite directions along a line of response, and a gamma ray pair detected within a coincidence time window is recorded as an annihilation event. The events acquired during a scan are reconstructed to produce images indicative of the distribution of the radionuclide and, hence, FDG uptake by the cells in the body.

Unfortunately, the patient, after administration of tracer, may be overcome with various emotions, such as anxiety with a patient who has never been scanned before, which may result in an increased heart rate and thus increased metabolism. Alternatively, the patient may move around which may increase muscle metabolism. For example, the patient may cough, which may increase metabolism in the abdominal muscles, or they get up and walk, which may increase metabolism in the leg muscles. Alternatively, the patient may consume a sugar containing food or beverage before the scan. The above represents non-limiting examples of physiological and behavioral states that may affect tracer uptake in a target region of interest.

The above, as well as other, physiological and/or behavioral states may impact uptake and distribution of the tracer in the body. As a consequence, the rate of tracer uptake, in general, may be higher than expected, an unexpected amount of tracer uptake may occur in regions other than the region of interest, which may decrease image contrast with respect to the region of interest, etc. The above-noted as well as other consequences may lead to a more difficult and/or incorrect interpretation of the images based on the tracer uptake shown in the images.

Aspects of the present application address the above-referenced matters and others.

According to one aspect, a method includes obtaining an image of a region of interest of a subject, wherein the image is generated with image data produced by an imaging system used to scan the subject, obtaining a signal indicative of a physiological state of the subject before the scan, and displaying both the image and data indicative of the physiological state.

In another aspect, a system includes a data packager that packages an image of a region of interest of a subject and data indicative of at least one of a physiological or a behavioral state of the subject together, wherein the image is generated with image data produced by an imaging system used to scan the subject and the state is obtained prior to scanning the subject.

In another aspect, a method includes obtaining a signal indicative of a physiological or behavioral state of a subject before a scan of the subject, adapting or changing a planned scan protocol for the scan based on the signal, and scanning the subject based on the adapted or changed scan protocol.

In another aspect, a method includes obtaining a signal indicative of a physiological or behavioral state of a subject before a scan of the subject, generating supplemental data indicative of an affect of the state on tracer uptake in the subject state based on the signal, and displaying the image with the supplemental data.

In another aspect, a method includes obtaining a signal indicative of a physiological or behavioral state of a subject before a scan of the subject, generating a correction for an image or image data from the scan based on the signal, wherein the correction corrects for an anticipated affect of the state on tracer uptake in the subject state, and correcting the image or image data based on the correction.

In another aspect, a method includes correcting, via a processor, a tracer uptake value for a target region of interest based on a tracer uptake correction factor.

In another aspect, a system includes a processing component and a target ROI tracer uptake corrector. The processing component includes a target ROI tracer uptake determiner that determines a tracer uptake value for a target region of interest, a non-target ROI tracer uptake determiner that determines a concurrent tracer uptake value for at least one non-target region of interest, and a process tracer uptake determiner that determines a concurrent tracer uptake value for at least one physiological process. The target ROI tracer uptake corrector corrects the tracer uptake value for the target region of interest based on at least one of the concurrent tracer uptake value for the at least one non-target region of interest or the concurrent tracer uptake value for the at least one physiological process.

Still further aspects of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

The following generally relates to using information indicative of a subject's physiological and/or behavioral state before and/or during a functional or non-functional imaging procedure in connection with the procedure. As described in greater detail below, this may include providing such information and/or supplemental information based thereon with image data and/or an image(s) generated therefrom. Additionally or alternatively, this may include using the physiological and/or behavioral state information to adapt or change the protocol for the imaging procedure. Additionally or alternatively, this may include using the physiological and/or behavioral state information to correct the image data and/or image(s). In other embodiments, the physiological and/or behavioral state information may be alternatively used.

Figure 1:
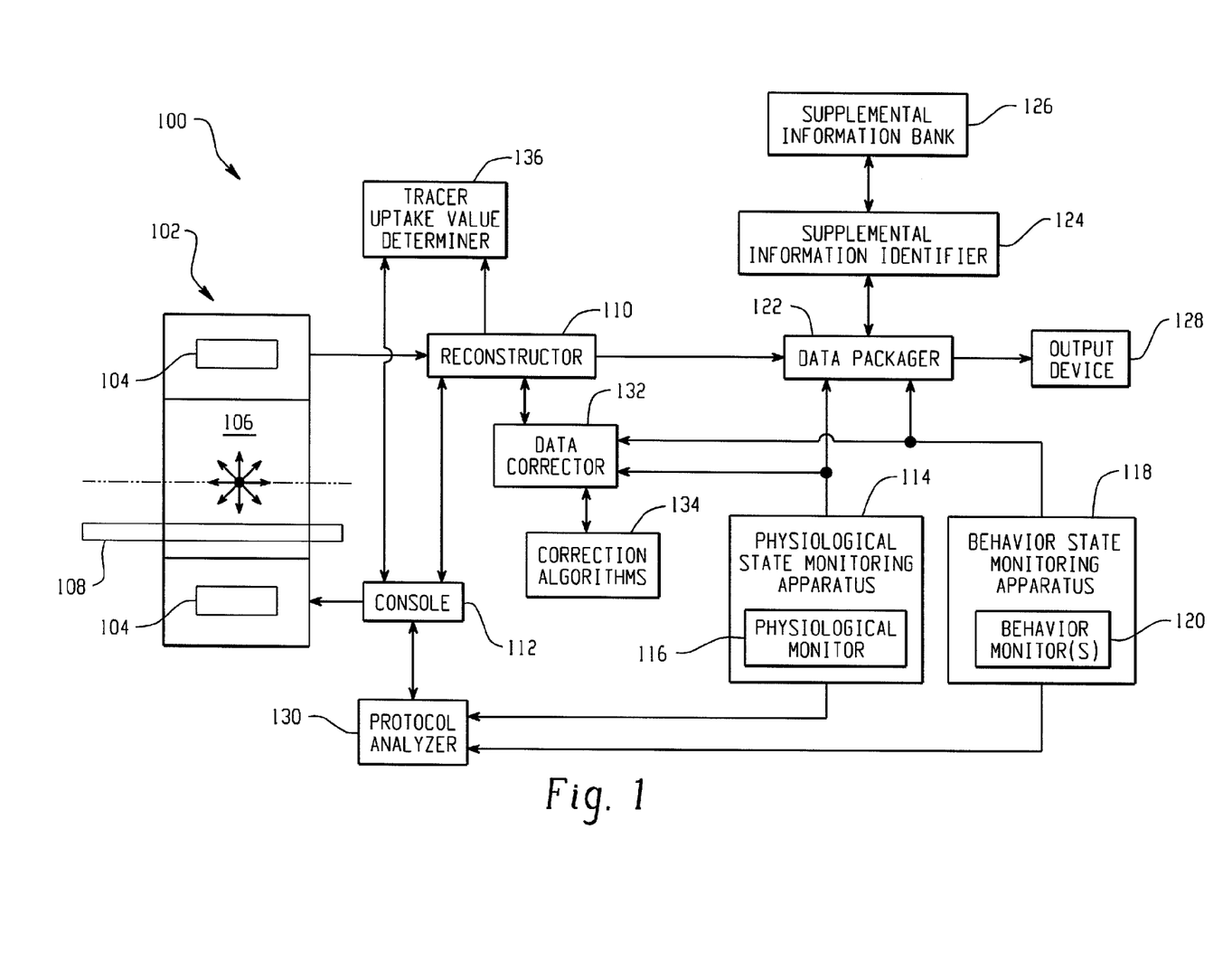
FIG. 1 illustrates an example imaging system.

Initially referring to FIG. 1, a system 100 includes a scanner 102, which may be a positron emission tomography (PET), single photon emission computed tomography (SPECT), magnetic resonance (MR), computed tomography (CT), ultrasound (US), or other scanner. For explanatory purposes and sake of brevity, the scanner 102 is described in relation to a PET scanner.

The scanner 102 includes a gamma radiation sensitive detector array 104 disposed about an examination region 106 along a longitudinal axis in a generally annular arrangement. A detector may include one or more scintillation crystals and corresponding photosensors, such as photomultiplier tubes, photodiodes, etc. A crystal produces light when struck by a gamma ray, and a photosensors receives the light and generates a signal indicative thereof. The detector array 104 detects gamma radiation characteristic of positron annihilation events occurring in the examination region 106.

When configured to operate in list mode, the signal is processed to generate a list of detected annihilation events, including information such as a time at which an event is detected, as well as a position and orientation of a corresponding line-of-response (LOR). When configured with time-of-flight (TOF) capabilities, an estimate of the position of the annihilation along the LOR is also provided. A PET reconstructor 110 reconstructs the data using a suitable reconstruction algorithm and generates image data and/or one or more images indicative of the distribution of the decay in the scanned object or subject.

A support 108 supports an object or subject, such as a human or animal patient, to be imaged in an examination region 106. The support 108 is longitudinally movable in coordination with operation of the system so that the object or subject can be scanned at a plurality of longitudinal locations.

A computer serves as an operator console 112 that includes a human readable output device such as a monitor or display and one or more input devices such as a keyboard and mouse. A processor of the console 112 executes software or computer readable instructions encoded on computer readable medium, which allows the operator to perform functions such as selecting and/or modifying imaging protocols, initiating, pausing and terminating scans, viewing and/or manipulating the projection and/or image data, etc.

The system 100 also includes a physiological state monitoring apparatus 114 with one or more physiological monitors 116. Suitable physiological monitors include, but are not limited to, a heart rate monitor, a blood pressure monitor, a respiratory monitor, a temperature monitor, a humidity monitor, a blood sugar monitor, and/or other physiological monitor and/or other device such as a accelerometer, transducer, etc. which can detect a signal indicative of a physiological parameter.

In one instance, at least one of the monitors 116 is a portable monitor that can be carried by the patient. For example, at least one of the monitors 116 may be incorporated into a wrist band, a removable adhesive patch, an arm cuff, a finger cuff, an ear clip, a belt, clothes, or other device worn by the patient. It can also be incorporated into a cell phone, a pager, a portable media (e.g., music, video, etc.) player, and/or other portable device.

Such a monitor(s) 116 can be installed on the subject a suitable time (e.g., 12 to 24 hours) prior to administration of a tracer, which allows for obtaining such information before tracer administration, as well as during a scan with the scanner 102. Another of the monitors 116 may be wall mounted, incorporated into a moveable or transportable device configured with wheels or otherwise, or placed on a table or other surface. The monitor 116 includes a port for communication or the like for data communication via a cable and/or wireless (e.g., IR, RF, optical, etc.) medium.

The system 100 optionally includes a behavior state monitoring apparatus 118 with one or more behavior monitors 120. Such a monitor includes, but is not limited to, a camera, a video recorder, a microphone, a motion detector, and/or other behavior monitor or device that can detect a signal indicative of behavior. Generally, cameras, video recorders, and the like are mounted to a wall, a ceiling, a tripod, etc., or placed on a surface. A microphone can be carried by the subject like a physiological monitor 116 or located within proximity of the subject. Motion detectors also may or may not be carried by the subject.

Both monitoring apparatuses 114, 118 also include a clock, a timer, or the like. As such, the information obtained thereby can be time stamped.

A data packager 122 variously packages image data or an image(s) generated by the scanner 102 based on information from the physiological state monitoring apparatus 114 and/or the behavior state monitoring apparatus 118. For example, in one instance the data packager 122 superimposes, overlays, annotates or otherwise combines information such as heart rate, ECG signal, respiratory rate, body temperature, etc. from the apparatuses 114 and/or 118 over one or more images.

Additionally or alternatively, the data packager 122 generates a message or report that includes such information. The message or report can be included in a file that is separate but linked to or associated with image data or image, a field in an electronic data pack (e.g., in DICOM (Digital Imaging and Communications in Medicine) or other electronic transmission format), etc. Additionally or alternatively, the data packager 122 generates new data including at least a subset of the image data and/or the image and a subset of the monitored information or message.

Additionally or alternatively, the data packager 122 packages supplemental data with image data or images. A supplemental information identifier 124 identifies and provides suitable supplemental data based on the information from the physiological state monitoring apparatus 114 and/or the behavior state monitoring apparatus 118. A supplemental information bank 126 stores supplemental data. Based on the information from the apparatuses 114, 118, the supplemental information identifier 124 may identify and obtain a message in the supplemental information bank 126 that states "the subject had an elevated heart rate during the tracer uptake period," "the subject moved around frequently after tracer administration," "the subject ingested sugar before tracer administration," etc.

The supplemental information bank 126 may include one or more look up tables, rules, or the like that map the information from apparatuses 114, 118 or information derived therefrom to one or more such messages. The look up tables can be manually or auto/semi-automatically (e.g., via machine learning or otherwise) generated based on historical data about the current subject and/or other subjects such as other subjects receiving a similar tracer, being scanned with a similar imaging protocol, having similar biological characteristics such as same gender, age, weight, height, race, etc., having a similar pathology, etc. In another instance, computer implementable logic may be provided to derive such information based on the information from apparatuses 114, 118.

Other information that can be packaged with and/or utilized with the image data and/or image includes information provided by the subject and/or observed. For instance, the subject may be asked various questions relating to emotions, physiological states, behavior, etc., and this information can be packaged and/or utilized with the image data and/or image. In another instance, such information can be provided by a clinician, a family member, and/or other person who observed the subject. In addition, information related to patient preparation and the imaging procedure may be packaged with the image data and/or images. Alternatively, such information is separately provided with the image data and/or images.

An output device 128 presents and/or transfers packaged data. In one instance, the output device 128 includes a computer display and the packaged data is visually presented on the display. In another instance, the output device 128 includes a filmer, a printer, or the like. In yet another instance, the output device 128 includes a data communications port for conveying the packaged data via cable or wirelessly (e.g., via infrared (IR), radio frequency (RF), or optical media) over a network, a bus, or the like. In still another instance, the output device 128 includes portal memory and/or a device that can write to portal memory.

A protocol analyzer 130 analyzes the planned imaging protocol and the information from apparatuses 114, 118. Such analysis may include predicting whether and/or how the information from apparatuses 114, 118 may affect the information in the image data or image based on the selected protocol. In response, the protocol analyzer 130 may identify and provide suggested changes to suitably adapt the protocol. For example, the protocol analyzer 130 may send a notification to the console 112 indicating that the operator should consider delaying the scan by time T or prolonging the scan time based on the information from apparatuses 114, 118.

In another example, the notification may additionally or alternatively include alternative protocols. Such protocols can be determined via pattern matching, inferences, machine learning, and the like. In yet another example, the notification may indicate that the operator should consider canceling the scan and rescheduling the procedure. Such information can be presented to the user via the console 112 and/or otherwise. In one instance, the protocol can be changed by a user selecting the change or alternative protocol or confirming termination of the scan via an input device of the console 112. Such interaction may be through a graphical user interface (GUI), a command line interface, and/or other interface.

A data corrector 132 employs the information from apparatuses 114, 118 to correct image data and/or images. The correction can be based on a pre-determined algorithm such as an algorithm included in a correction algorithm bank 134. Such algorithms can be based on historical data and/or correlations between physiological and/or behavioral data and information provided in the image data and images. Such data may be generated based on a pool of information related to the subject being scanned and/or other subjects such as subjects receiving a similar tracer, being scanned with a similar imaging protocol, having similar biological characteristics such as same sex, weight, height, race, etc., having a similar pathology, etc. In another instance, computer implementable logic may be provided to derive such information based on the information from apparatuses 114, 118. This can be through simulation and/or otherwise. Pre-trial information can also be used.

In the context of the above non-limiting example, feedback or information indicative of a subject's physiological and/or behavioral parameters before and/or during an imaging procedure can be used to facilitate conducting the procedure, including facilitating interpreting images, adapting or change the imaging procedure protocol, correcting the image data and/or images, etc.

It is to be appreciated that in other embodiments one or two of the data packager 122 and corresponding components 124, 126, the protocol analyzer 130, and/or the data corrector 132 and corrections algorithms 134 can be omitted.

In addition, the data packager 122, the supplemental data components 124, 126, the protocol analyzer 130, the data corrector 132, and/or the corrections algorithms 134 can be located separate from the scanner 102, for example, as part of a separate system(s) in the same or different examination room, or may be part of the scanner 102, for example, implemented via software and/or hardware in connection with the console 112.

The system 100 also includes a tracer uptake value determiner 136 that determines a tracer uptake value for a target region of interest. As described in greater detail below, in one instance the tracer uptake value determiner 136 corrects the tracer uptake value for the target region of interest based on concurrent tracer uptake by non-tissue and/or processes, which can be determined base on imaging data and/or non-imaging data.

Figure 2:
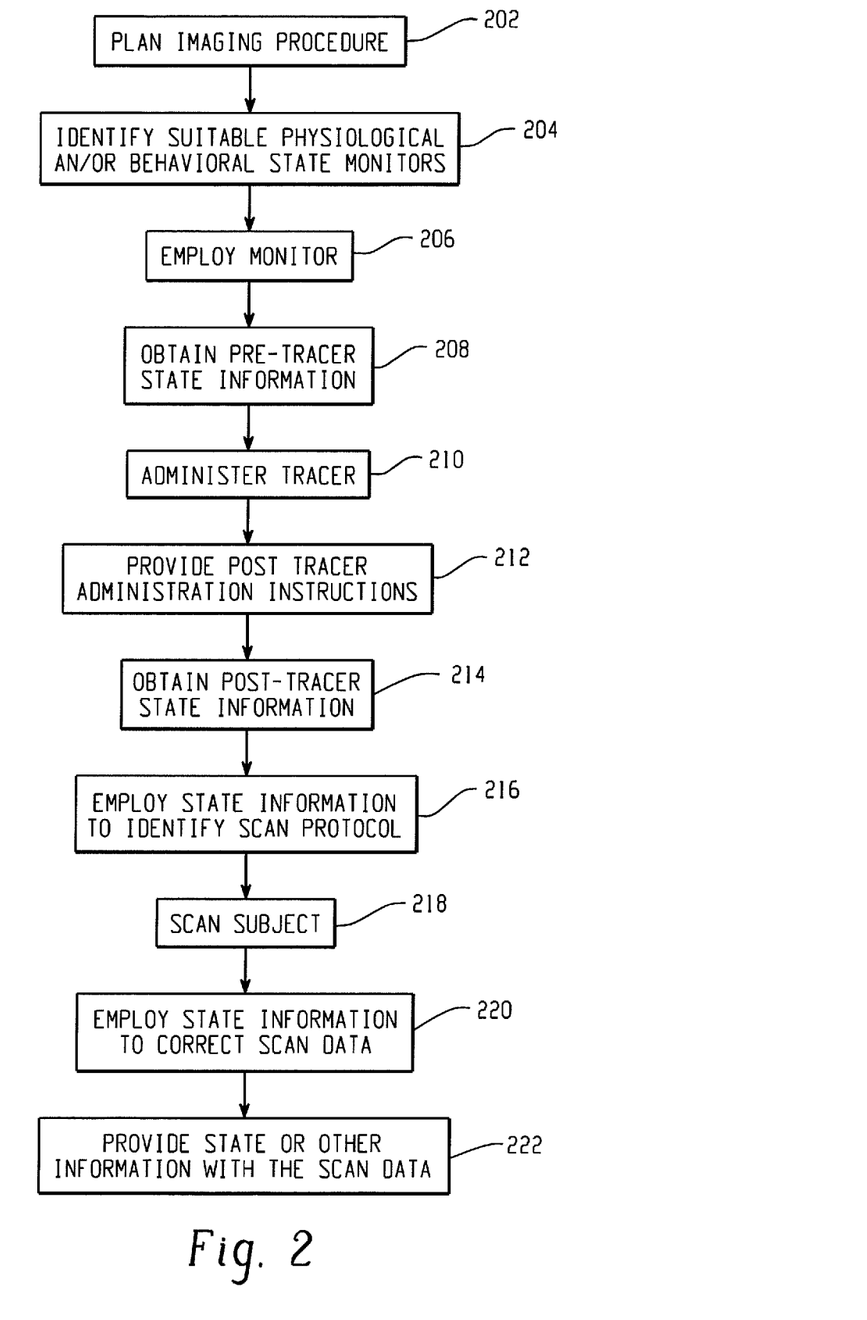
FIG. 2 illustrates an example method for using physiological and/or behavioral state information in connection with imaging with the imaging system of FIG. 1.

FIG. 2 illustrates a method of using the system 100 in connection with a functional PET imaging procedure. As noted above, the system 100 may alternatively include a scanner based on a different imaging modality and be used for non-functional imaging.

At 202, a functional PET imaging procedure is planned for a subject.

At 204, a suitable monitor(s) is identified for the subject. As discussed herein, the monitor may be configured to determine one or more physiological parameters and the behavior of the subject before and/or after the scan.

At 206, the identified or selected monitor(s) is installed on the subject as described herein, for example, through objects worn or carried by the subject, or placed within suitable proximity to monitor the subject at some predetermined time before the examination.

At 208, pre-tracer administration physiological and/or behavioral states are obtained. This information may be used as a baseline or reference information. Historical information such as that obtained during periodic physical exams or otherwise can also be used as baseline or reference information.

At 210, a tracer is administered. In this example, the tracer is FDG. Other suitable PET tracers include, but are not limited to, fluorothymidine (FLT), fluorothyltyrosine (FET), fluoromisonidazole (FMISO), O15-H2O, and fluoroazomycinarabinofuranoside (FAZA), etc. When another imaging modality is used, a suitable tracer for that modality is administered.

At 212, the subject is instructed as far as how to prepare for the scan. This includes informing the subject of movement that subject should attempt to avoid, food and/or beverage restrictions, etc.

At 214, post tracer administration physiological and/or behavioral states are obtained using the monitors.

At 216, the pre and/or post physiological and/or behavioral states are used to identify possible imaging protocol adaption and/or alternatives, if any. This is described in greater detail in connection with FIG. 4 below. This act may be omitted.

At 218, the subject is scanned, and image data and/or one or more images are generated.

At 220, the physiological and/or behavioral states are employed to correct the scan data or resulting image data and/or images. This is further described in greater detail in connection with FIG. 5 below. This act may also be omitted.

At 222, the physiological and/or behavioral states, information derived therefrom, and/or information such as behavioral observations made about the subject, questionnaire answers from the subject, etc. are provided for review along with the image data and/or image(s). This is further described in greater detail in connection with FIG. 3 below.

Figure 3:
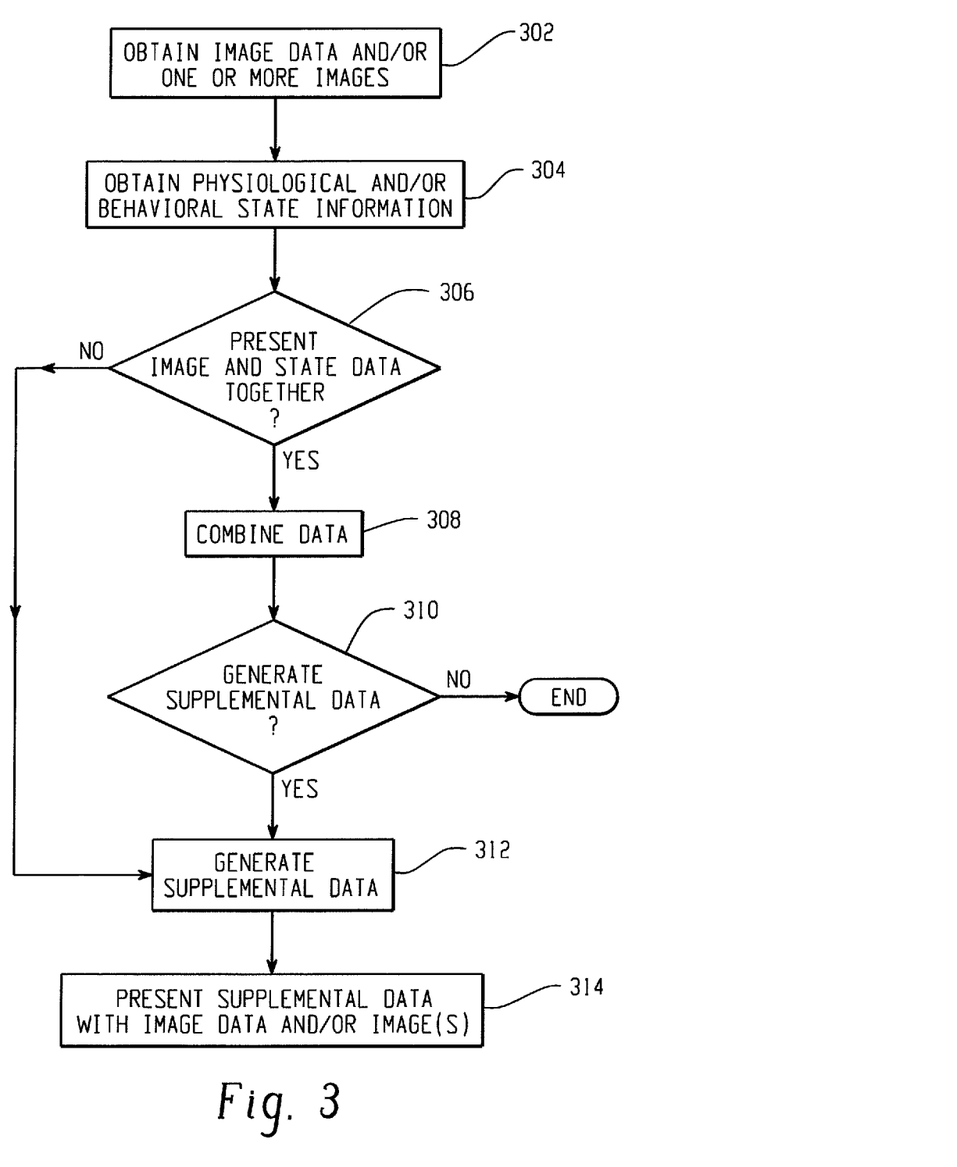
FIG. 3 illustrates an example method for providing physiological and/or behavioral state information with an image generated with data produced by the imaging system of FIG. 1.

FIG. 3 illustrates a method for providing information with image data and/or images.

At 302, image data and/or an image(s) are obtained. Such information can be obtained from the scanner 102, a data repository, and/or otherwise.

At 304, physiological and/or behavioral state information is obtained. Such information can be obtained from the physiological and behavior state apparatuses 114, 118, a data repository, and/or otherwise.

At 306, it is determined whether the image data and/or image(s) and the physiological and/or behavioral state information are to be presented together.

If so, then at 308 the physiological and/or behavioral states and image data and/or images are combined. This may include superimposing, overlaying, annotating, etc. the data. For example, an image may be created to include the original image, a pre tracer administration or baseline ECG signal or heart rate value, and an ECG or heart rate value after administration of a tracer. A clinician interpreting the image may use the pre and post tracer administration ECG or heart rate information when interpreting the image.

At 310, it is determined whether supplemental data is to be generated based on the physiological and/or behavioral state information. If not, supplemental information is not generated.

If so, then at 312 supplemental data is generated based on the physiological and/or behavioral state information. As discussed herein this may include identifying or deriving suitable messages to provide or display with the image data and/or image(s). For example, if the subject was observed walking around after tracer administration, the message might state "the subject walked around after tracer administration."

At 314, the message is provided with the image data and/or image(s). This may include providing a separate file containing the message and/or combining the message with the image data and/or image(s).

If at 306, it is determined that the image data and/or image(s) and the physiological and/or behavioral state information are not to be combined, then acts 312 and 314 are performed.

Figure 4:
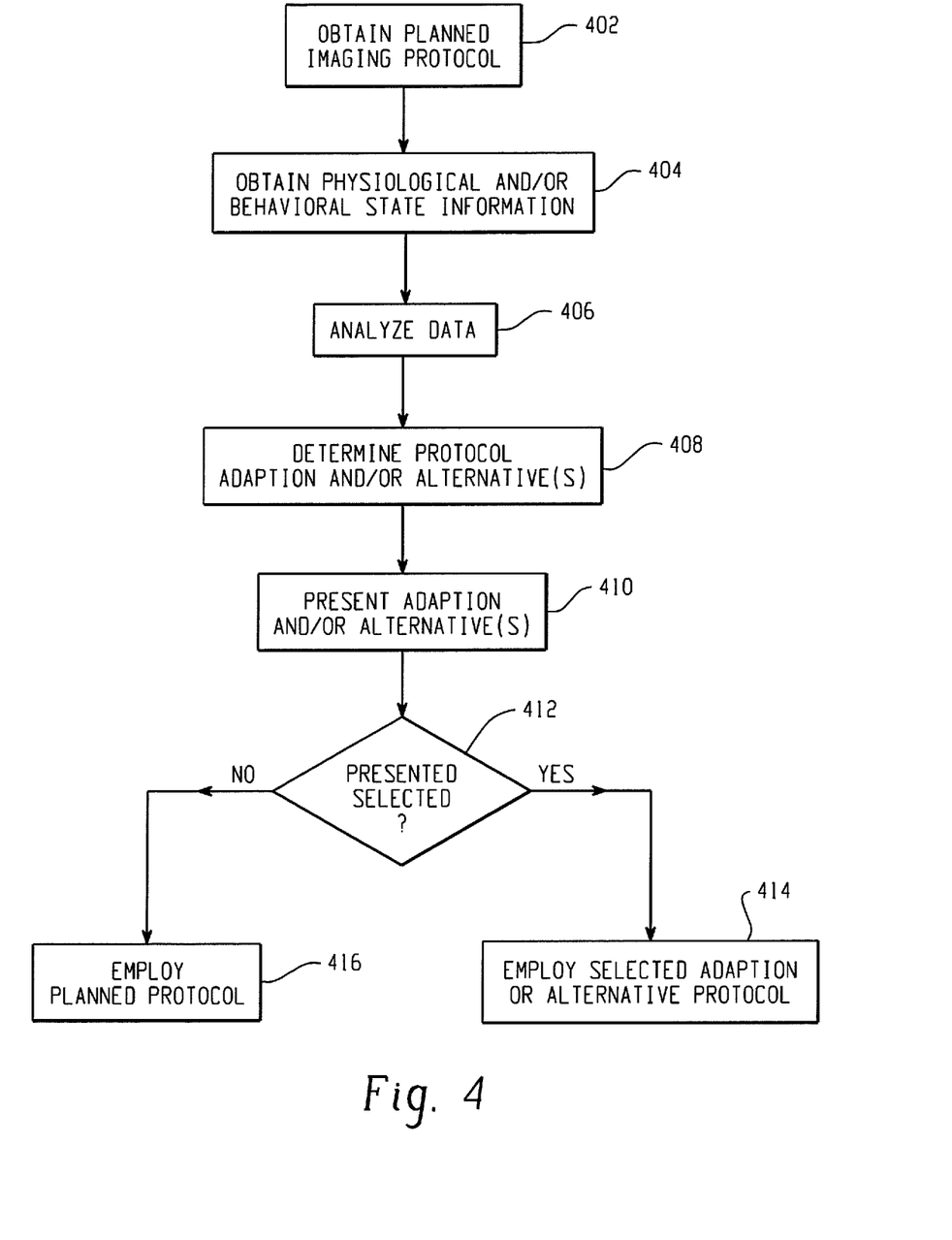
FIG. 4 illustrates an example method for using physiological and/or behavioral state information for adapting or changing the imaging protocol used with the imaging system of FIG. 1.

FIG. 4 illustrates a method for using the monitored physiological and/or behavioral state to adapt or change the imaging protocol.

At 402, the planned imaging protocol is obtained. Such information can be provided by the console 112 and/or otherwise.

At 404, physiological and/or behavioral state information is obtained. Such information can be obtained from the physiological and behavior state apparatuses 114, 118, a data repository, and/or otherwise.

At 406, the physiological and/or behavioral state information is analyzed in light of the planned imaging protocol.

At 408, a protocol adaption and/or one or more alternative protocols are identified. As noted above, this may include extending the time before the scan, extending the scan time, etc.

At 410, the identified protocol adaption and/or one or more alternative protocols are presented for using/selection.

At 412, it is determined if a presented adaption or alternative is selected.

If so, then at 414 the scan is performed base on the adaption or alternative.

If not, then at 416 the planned protocol is used.

Figure 5:
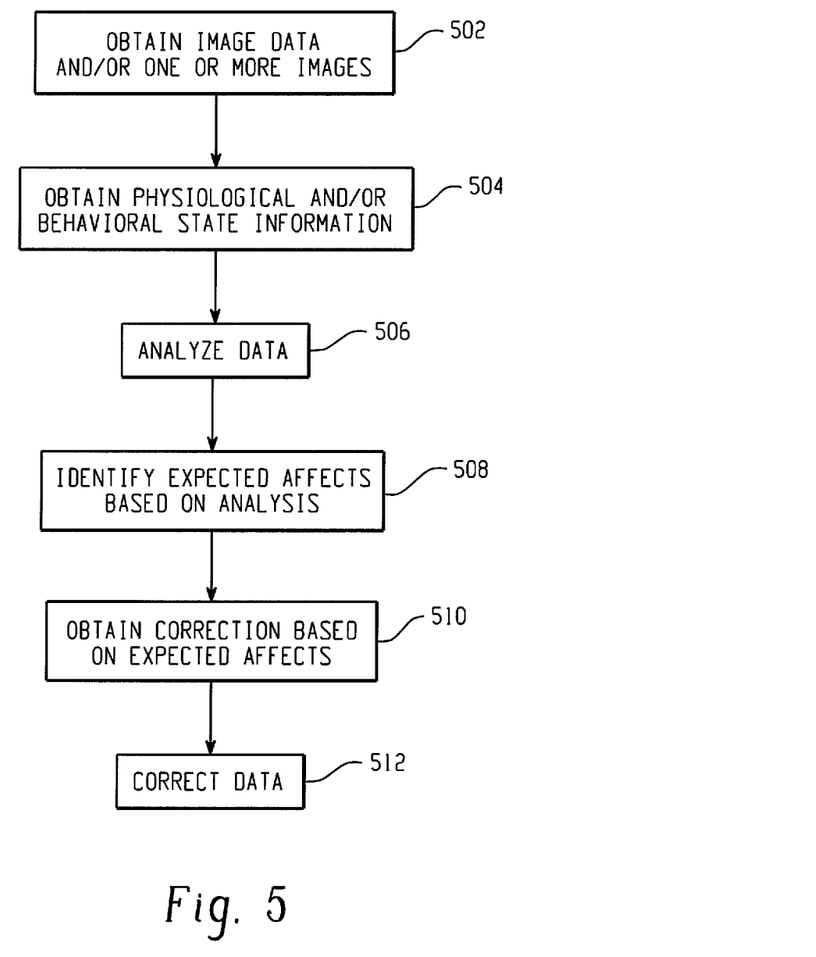
FIG. 5 illustrates an example method for using physiological and/or behavioral state information for correcting image data and/or an image(s) generated with data produced by the imaging system of FIG. 1.

FIG. 5 illustrates a method for using the monitored physiological and/or behavioral state to correct image data and/or an image(s).

At 502, image data and/or an image(s) are obtained. Such information can be obtained from the scanner 102, a data repository, and/or otherwise.

At 504, physiological and/or behavioral state information is obtained. Such information can be obtained from the physiological and behavior state apparatuses 114, 118, a data repository, and/or otherwise.

At 506, the physiological and/or behavioral state information is analyzed.

At 508, expected effects based on the analysis of the state information are identified. As discussed herein, this can be achieved based on historical data, simulated data, pre-trial data, and/or other data.

At 510, a correction based on expected effects is obtained. As discussed herein, the correction can be based on a predetermined algorithm and/or derived using machine learning or other techniques.

At 512, the image data and/or image(s) is corrected using the correction.

Figure 6:
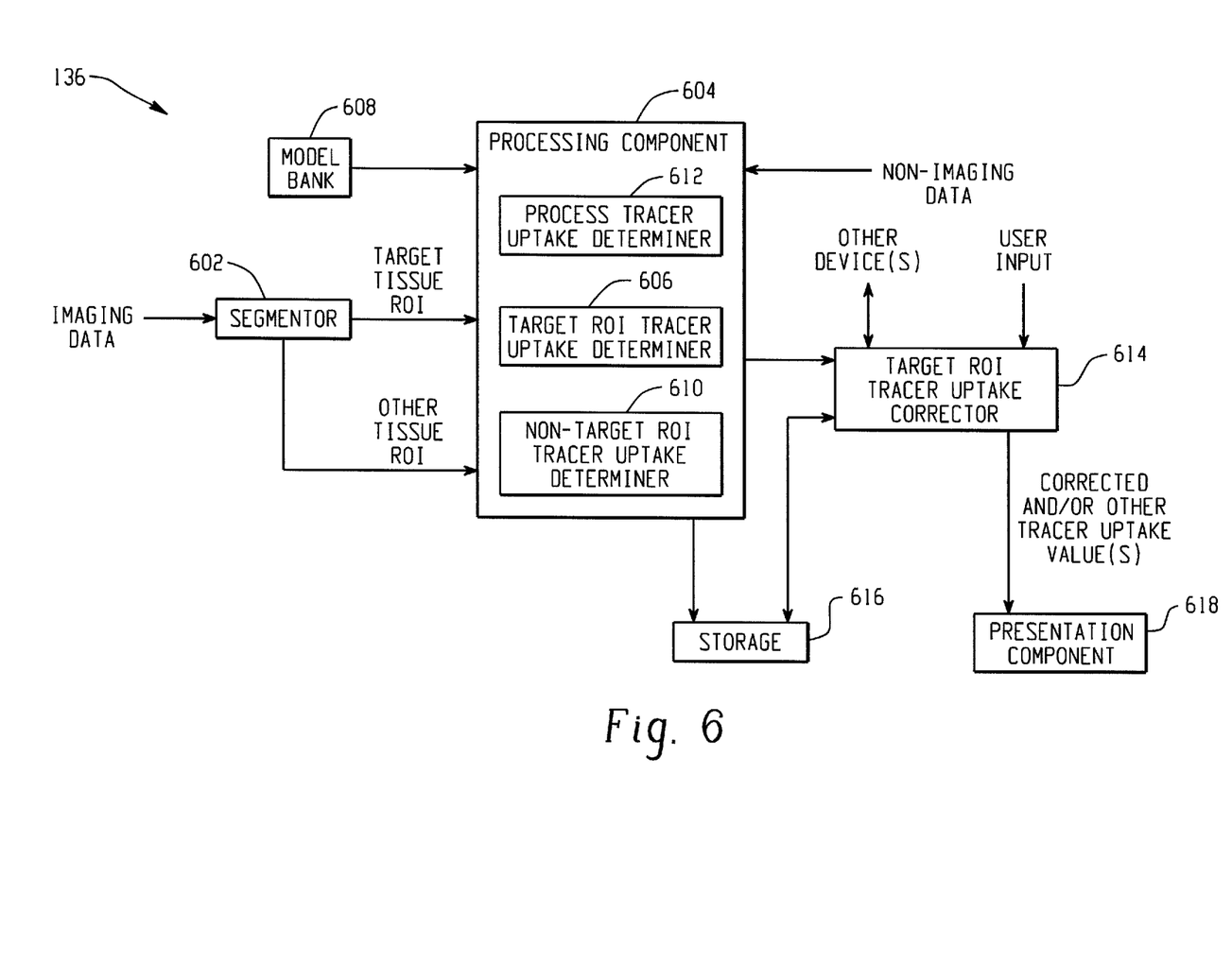
FIG. 6 illustrates an example tracer uptake value determiner.

FIG. 6 illustrates an example of the tracer uptake value determiner 136. A segmentor 602 facilitates segmenting imaging data (e.g., PET, SPECT, MRI, CT, US and/or imaging data) into one or more regions of interest (ROIs). Where the imaging data includes multi-modality information, the imaging may be registered or otherwise correlated. The one or more ROIs may represent the entirety or sub-portions of different anatomical tissue such as brain, liver, kidney, lungs, bladder, etc.

In one embodiment, a user interacts with the segmentor 602 through an interface such as a graphical user interface of a console or web application that is presented on a display. In this embodiment, the user provides input that facilitates identifying one or more regions of interest, including, but not limited to, target tissue and/or other tissue of interest. The input can be provided via a mouse, a pointer, keyboard, or other device.

In one instance, the input identifies a perimeter of the region of interest. In yet another instance, the input identifies a portion of the perimeter, and the segmentor 602 determines a remaining portion of the perimeter. In yet another instance, the input identifies tissue of interest (e.g., brain), and the segmentor 602 identifies a region of interest in the imaging data corresponding to the identified tissue of interest. Examples of suitable algorithms for doing so include mesh, growing and/or other algorithms.

Where the segmentor 602 automatically identifies ROIs, the input may include indicia identifying the tissue of interest and validation information for validating and rejecting automatically determined ROIs. It is also to be appreciated that user can modify a segmentor 602 defined region of interest, including increasing or decreasing size, changing the shape, etc.

A processing component 604 includes a target ROI tracer uptake determiner 606, a non-target ROI tracer uptake determiner 610, and a physiological process tracer uptake determiner 612. These components can determine tracer uptake value based on imaging and/or non-imaging data. The imaging data can include segmented or partially segmented data from the segmentor 602 and/or imaging data from a data repository and/or another device. The non-imaging data includes laboratory data, physical state, physical activity, vital signs, and/or other information, which can be obtained from a data repository and/or another device and/or entered by a clinician.

By way of non-limiting example, imaging data from a Picture Archiving and Communication System (PACS) can be transferred (via Digital Information Imaging and Communications in Medicine (DICOM) or other format) to the processing component 604 and used thereby to determine tracer uptake values. In another example, non-imaging data from a laboratory information system (LIS) (e.g., blood chemistry, glucose level, etc.) and/or other non-imaging data (e.g., vital signs, patient activity, etc.) can be obtained and utilized by the processing component 604. Other useful data repositories include, but are not limited to, a Radiology Information System (RIS), a Hospital Information System (HIS), etc.

Other suitable non-imaging information includes biomarkers. For example, dietary information like consumption of alcohol and rich food prior to the imaging studies are represented in blood markers like Glutamic-Pyruvic Transaminase (GPT), Glutamic-Oxaloacetic Transaminase (GOT), Gamma-Glutamyl Transpeptidase (Gamma-GT, GGT) for liver function, creatinine for kidney function, insulin, glucose, blood alcohol. Depending on the tracer, other markers may be relevant. For example, for FMISO, a hypoxia tracer, the arterial oxygen saturation is a marker. For HED, an enervation tracer, the drug status (beta blockers) is a marker.

The target ROI tracer uptake determiner 606 determines a tracer uptake value for the identified target tissue based at least upon segmented imaging data corresponding to the target tissue. Where only a portion of the region of interest is captured in the imaging data, the tracer uptake value can be determined for the region of interest by estimating the volume of the region of interest via a model or otherwise and extrapolating the trace uptake value for the image portion to the estimated volume. Such models are stored in a model bank 608.

The non-target ROI tracer uptake determiner 610 determines tracer uptake values for segment regions of interest corresponding to tissue other than the target tissue. These regions may include regions of relatively higher tracer uptake and/or significant volume, although they may additionally or alternatively include other regions. Similar to above, where the imaging data represents only a portion of the tissue, a model or other algorithm can be employed to estimate the volume of the region of interest, and tracer uptake can be determine based on the tracer uptake value for the sub-portion and the estimated volume.

With tissue like muscle, which consumes tracer, the entirety of the tissue in the body generally is not scanned. In such an instance, the volume of the muscle may be estimated from a population mean model, via a look-up table (LUT) and/or mathematical function, stored in the model bank 608. For this, patient information like weight, size, height, width, circumflex, etc. can be evaluated and used to facilitate estimating the volume of muscle. As tracer uptake in muscle in different parts of the body may be different, the various factors used to determine the tracer uptake may be weighted.

In another example, tracer uptake values for a predetermined number of sub-regions of muscle can be determined. From this data, tracer uptake values for other sub-regions of the muscle can be determined and summed together to generate a tracer uptake value for muscle. In another example, the tracer uptake value for the muscle can be determined via extrapolating the tracer uptake value for the predetermined sub-regions. In yet another example, a mean value can be determined from the tracer uptake values for the sub-regions, and the mean value can be used as or used to determined the tracer uptake value for muscle. Again, the data may be weighted to take into account different uptake in different parts of the body.

The physiological process tracer uptake determiner 612 determines tracer uptake values for physiological processes. An example of such a process is urination. For such a process, the imaging protocols can take into account tracer accumulation in the bladder, which can degrade image quality. For example, in one instance the protocol may have the patient urinate prior to scanning. To estimate the amount of tracer lost by urination, the volume and/or weight of the urine is measured or estimated. In one instance, this includes having the subject urinate in a container and then measuring the weight of the filled container. In another instance, the subject is weighed before and after urination to determine the volume of urination. In either instance, the activity of expelled urine is estimated from the average activity in the segmented bladder.

A tracer uptake corrector 614 corrects the tracer uptake value generated by the target ROI tracer uptake determiner 606. In the illustrated embodiment, the tracer uptake corrector 614 corrects this tracer uptake value based on a correction factor such as concurrent tracer uptake values of other tissue and/or processes. The concurrent tracer uptake can be determined by the non-target ROI tracer uptake determine 610 and/or the process tracer uptake determiner 612. Generally, concurrent tracer uptake refers to tracer uptake by non-target tissue and/or processes, which reduces the amount of tracer available for uptake in the target tissue.

In one instance, the tracer uptake corrector 614 corrects the tracer uptake value through a mathematical function such as by subtracting the individual concurrent tracer uptake values (or a summation thereof) of non-target segmented tissue, processes, etc. from the target ROI tracer uptake value. The subtraction may or may not be weighted. The correction may also include normalizing the tracer uptake value based on the target tracer uptake value, the concurrent tracer uptake values for other tissue and/or processes, the injected tracer activity, levels of relevant markers, and/or other information.

A storage component 616 includes computer readable storage, which can be used to store tracer uptake and/or corrected tracer uptake values. The storage component 616 may include local and/or remote, non-portable and/or portable memory. A presentation component 618 presents the tracer uptake and/or corrected tracer uptake values, and/or imaging data and/or non-imaging data corresponding thereto. Such information can be variously presented, for example, in the form of tables, graphs, graphics, etc., showing the measured and/or the corrected tracer uptake values. The information can also be printed to paper and/or other tangible medium.

It is to be appreciated that the tracer uptake determiner 136 (and the components thereof) may be implemented through one or more computer processors that execute computer readable instructions stored in computer readable storage medium. As shown in FIG. 1, in one instance the tracer uptake determiner 136 is implemented via a computing apparatus remote to and in communication with the scanner 102. In another instance, the tracer uptake determiner 136 is implemented via the console 112 of the scanner 102.

Figure 7:
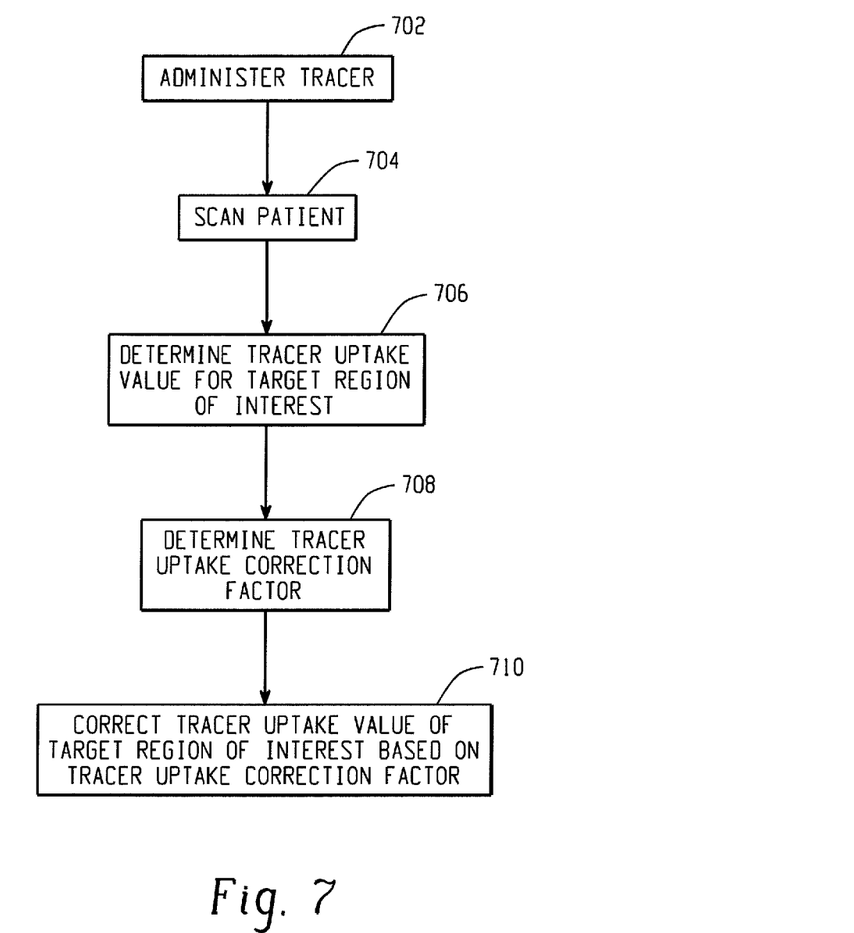
FIG. 7 illustrates an example method for correcting tracer uptake for a target region of interest based on concurrent tracer uptake for non-target regions of interest and/or processes.

FIG. 7 illustrates a method for correcting a tracer uptake value for a target region of interest.

At 702, a tracer is administered to a patient.

At 704, a perfusion scan is performed. The perfusion scan captures uptake and wash out of the tracer.

At 706, imaging data from the scan is processed to determine a tracer uptake value for the target region of interest. Models and/or non-imaging data can be used to facilitate determining the tracer uptake value.

At 708, a correction factor is generated for the tracer uptake value for the target region of interest. As described herein, in one instance this include processing imaging data and/or non-imaging data to determine concurrent tracer uptake values for one or more non-target regions of interest and/or processes, wherein concurrent tracer uptake generally refers to tracer uptake by non-target tissue and/or processes that reduces the amount of tracer available for uptake in the target tissue. Models may also be used to facilitate determining the tracer uptake value.

At 710, the tracer uptake value for the region of interest is corrected based on the correction factor. As noted herein, this may include subtracting the concurrent tracer uptake value from the tracer uptake value for the region of interest and/or otherwise processing the data such as normalizing the data.

The above may be implemented by way of computer readable instructions, which when executed by a computer processor(s), cause the processor(s) to carry out the described techniques. In such a case, the instructions can be stored in a computer readable storage medium associated with or otherwise accessible to the relevant computer.

It is to be appreciated that in one embodiment the tracer uptake value determiner 136 is omitted from FIG. 1. In another embodiment, the components 114-118 are omitted from FIG. 1.

The invention has been described with reference to various embodiments. Modifications and alterations may occur to others upon reading the detailed description. It is intended that the invention be constructed as including all such modifications and alterations insofar as they come within the scope of the appended claims or the equivalents thereof.

What is claimed is:

1. A method, comprising:
obtaining an image of a region of interest of a subject which contrasts a tracer uptake, wherein the image is generated with image data produced by an imaging system used to scan the subject;
obtaining a signal indicative of a physiological state of the subject before the scan and the physiological state impacts the tracer uptake before the scan;
determining an expected value of the tracer uptake for the region of interest;
determining a tracer uptake correction factor based on the physiological state before the scan; and
correcting the expected value of the tracer uptake for the region of interest based on the tracer uptake correction factor; and
concurrently displaying, via a display monitor, both the image and data indicative of the physiological state.

2. The method of claim 1, further comprising annotating the image with the physiological state.

3. The method of claim 1, wherein the physiological state is one of a heart rate, a respiratory rate, a body temperature, or a glucose level.

4. The method of claim 1, further comprising:
generating supplemental data based on the signal; and
displaying the supplemental data with the image.

5. The method of claim 4, wherein the supplemental data includes a message indicating a change in value of the physiological state, relative to a baseline value, that is greater than a predetermined threshold value.

6. The method of claim 4, further comprising overlaying the supplemental data on the image.

7. The method of claim 1, further comprising adapting or changing a planned scan protocol for the scan based on the signal indicative of a physiological state.

8. The method of claim 1, further comprising:
generating a correction for the image or the image data based on the signal indicative of a physiological state; and
correcting the image or the image data based on the correction.

9. The method of claim 8, wherein the correction is based on an expected affect of the physiological state on the image data or the image.

10. The method of claim 1, further comprising:
obtaining a second signal indicative of a behavioral state of the subject before the scan and the behavioral state includes at least one of coughing, walking, consuming a beverage, an emotional state, and consuming food; and
displaying second data indicative of the behavioral state with the image, and the second data impact the contrast of the image.

11. A system, comprising:
a data packager, implemented by a configured hardware processor, that packages an image of a region of interest of a subject and data indicative of a physiological state and a behavioral state of the subject together, wherein the image is generated with image data produced by an imaging system used to scan the subject and the physiological state and the behavioral state are obtained prior to scanning the subject; and
a physiological state monitoring apparatus that includes at least one physiological monitor that determines the physiological state of the subject prior to the scan and the physiological state is used to correct an expected tracer uptake contrasted in the image.

12. The system of claim 11, wherein the data packager overlays the data indicative of the physiological state and the behavioral state of the subject on the image.

13. The system of claim 11, further comprising:
a behavioral state monitoring apparatus that includes at least one behavior monitor that determines the behavioral state of the subject prior to the scan based on at least one of answers to a questionnaire, and an observation of patient external movement, and the behavioral state impacts a tracer uptake contrasted in the image.

14. The system of claim 11, further comprising:
a supplemental information identifier, implemented by the configured hardware processor, that identifies supplemental information based on the physiological state and the behavioral state, wherein the data packager packages the supplemental information with the image.

15. The system of claim 14, wherein the supplemental information identifier identifies the supplemental information by mapping the physiological state and the behavioral state to predetermined information in a supplemental information bank.

16. The system of claim 11, further comprising:
a protocol analyzer, implemented by the configured hardware processor, that determines a modification to a scan protocol for the scan or an alternative scan protocol for the scan based on a planned scan protocol and the physiological state and the behavioral state.

17. The system of claim 11, further comprising:
a data corrector, implemented by the configured hardware processor, that determines an image or image data correction based on a planned protocol and the physiological state and the behavioral state and corrects the image or the image data based on the correction.

18. The system of claim 11 wherein the physiological or behavioral state includes state information obtained after administration of a tracer and prior to the scan and the state information changes expected values of an uptake of the tracer in the subject.

19. The system of claim 18, wherein the physiological or behavioral state includes state information obtained prior to administration of the tracer to the subject and the state information changes expected values of an uptake of the tracer in the subject.

20. A method, comprising:
obtaining a signal indicative of a physiological state and a behavioral state of a subject before a scan of the subject;
generating supplemental data indicative of an affect of the physiological state and the behavioral state on an expected tracer uptake in the subject state based on the signal; and
displaying an image concurrently with the supplemental data.

* * * * *